United States Patent [19]

Berry

[11] Patent Number: 4,836,188

[45] Date of Patent: Jun. 6, 1989

[54] INSTRUMENT FOR ILLUMINATED STERESCOPIC VIEWING OF BODY CAVITIES

[76] Inventor: Yale J. Berry, 134 Clinton Rd., Brookline, Mass.

[21] Appl. No.: 860,043

[22] Filed: May 6, 1986

[51] Int. Cl.⁴ .................. A61B 1/06; G02B 23/02; G02B 27/14

[52] U.S. Cl. ........................... 128/6; 128/23; 350/145; 350/146; 350/171

[58] Field of Search ............... 128/6, 4, 23; 350/514, 350/515, 516, 517, 23, 145, 146, 171

[56] References Cited

U.S. PATENT DOCUMENTS

| | | | |
|---|---|---|---|
| 2,639,653 | 5/1953 | Fischer | 350/516 X |
| 3,512,860 | 5/1970 | Hansen | 350/516 |
| 3,520,587 | 7/1970 | Tasaki et al. | 350/515 |
| 4,196,966 | 4/1980 | Malis | 128/23 |
| 4,430,996 | 2/1984 | Bonnet | 128/4 X |
| 4,593,682 | 6/1986 | Heckele | 128/6 |

*Primary Examiner*—William H. Grieb
*Attorney, Agent, or Firm*—Rines and Rines Shapiro and Shapiro

[57] ABSTRACT

A multi-prism optical viewing instrument is provided for enabling stereoscopic viewing down tubular and/or deep body channels or cavities, such as the ear canal, nose, vagina, etc., too narrow to permit of viewing with both eyes, and while providing illumination down the channel or cavity without obstruction of the field of view.

5 Claims, 1 Drawing Sheet

INSTRUMENT FOR ILLUMINATED STERESCOPIC VIEWING OF BODY CAVITIES

The present invention relates to methods and instruments for enabling illuminated viewing within long, thin, narrow and/or deep body cavities or openings, as for examining and/or surgery within, for example, the ear canal, nose vagina, bowel, or other deep body cavities.

Present-day devices useful for such purposes operate simply by reflecting a beam of light from an external light source into such a tubular channel and allowing the viewer either to view along the channel through a one-way mirror or through a regular two-way mirror with a hole in it. An example of one such instrument is the A.O. Indirect Opthalmoscope of American Optical.

The employment of such rudimentary optical devices, however, has posed several problems which have been heretofore considered inherently necessary to endure. First, as it is not physically possible to look into a narrow tubular structure with both eyes simultaneously, long tubes such as the ear canal, nose, vagina, etc. are usually examined by the vision of one eye, with the limitations of monocular vision. Secondly, even with illuminated monocular inspection, it is most desirable to provide for ready optical enhancement or magnification of the area under examination.

An object of the present invention, accordingly, is to provide a new and improved inspection instrument that admirably obviates the above-described and other limitations of prior body cavity inspection apparatus and the like, and enables three-dimensional illuminated vision within small, narrow tubular structures with the attendant depth perception and other advantages of stereoscopic examination.

A further object is to provide in such an improved instrument, facility for varying magnification within such tubular structures during stereoscopic viewing.

Still another object is to provide a novel surgical and examining three-dimensional illuminated instrument particularly useful for otolaryngology, gynecology and proctology.

Other and further objects will be explained hereinafter and are more fully delineated in the appended claims.

In summary, however, from one of its important aspects, the invention embraces an instrument for illuminated stereoscopic examination of body cavities and the like, comprising a source of light, an optical system, and headgear means for supporting said source of light and said optical system on the head of an examiner, said optical system including means for directing light from said source away from the head of the examiner and toward a body cavity along a path substantially midway between the eyes of the examiner, means for splitting light reflected from said body cavity toward the head of the examiner along sad path into two beams of light, and means for directing said two beams of light toward the eyes of the examiner, respectively, said source of light being disposed relative to said optical system so as to avoid obstruction of the examiner's view of said body cavity through said optical system. Preferred and best mode embodiments and details are later presented.

The invention will now be described with reference to the accompanying drawings, FIG. 1 of which is a partial top elevation of the prism components of instruments designed to practice the invention;

Figure 1:
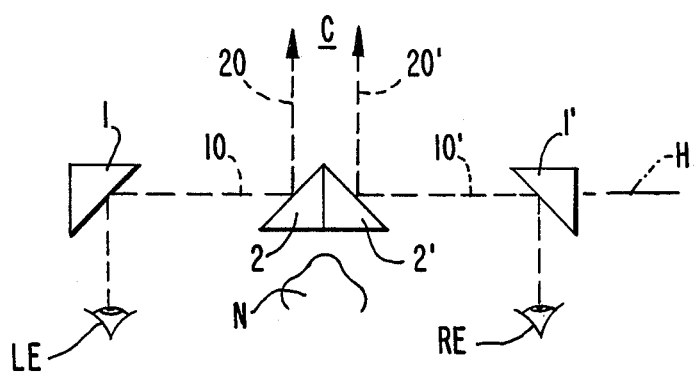

Referring to FIG. 1, a first pair of prisms 1 and 1' is shown mounted substantially on a horizontal axis H in front of the face of the examiner with the prisms separated by the distance between the eyes; the prism 1 being mounted in front of the left eye LE, and the prism 1' in front of the right eye RE. Each prism is respectively oriented to direct the field of vision of the respective eyes inwardly toward the nose N and the opposite eye, as schematically illustrated by light-ray dash lines 10 and 10', respectively. Mounted in front of the nose N centrally between the eyes and substantially along the horizontal axis H, is a second pair of juxtaposed, back-to-back, oppositely mounted prisms 2, 2' oriented further to direct the rays 10, 10' forwardly of the nose toward the channel C that is to be viewed (such as, for example, an ear canal or the nose), as shown by the respective dash lines 20 and 20'. The prisms 2, 2' are adjusted so that the parallel paths 20 and 20' are closely separated, of the order of several millimeters or so, to provide adjacent stereoscopic fields of vision for the eyes.

Figure 2:
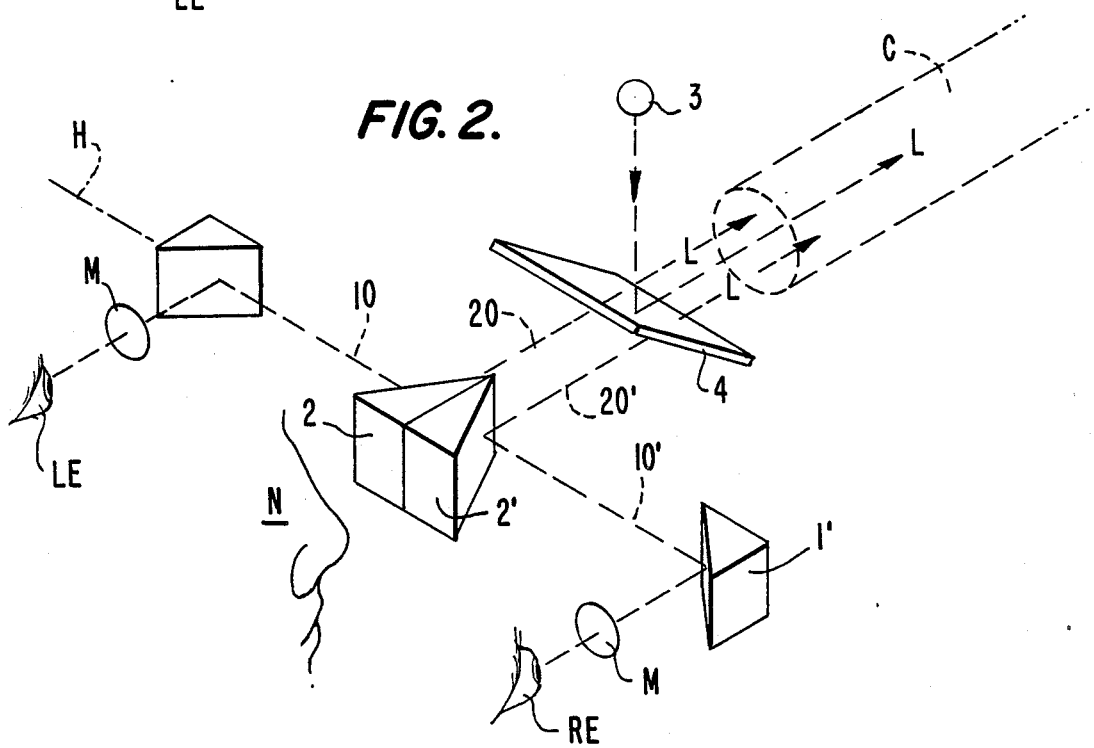
FIG. 2 is an isometric schematic view of the instrument of FIG. 1.
Figure 3:
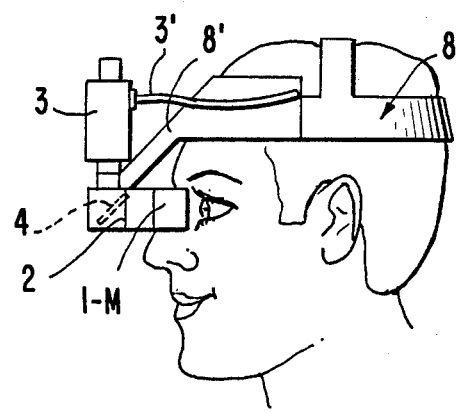
FIG. 3 is a view of the instrument mounted as examiner's headgear.

Further in accordance with the technique of the invention, illumination is provided down the channel C, as more particularly shown in FIGS. 1 and 2. This is effected by providing an illumination source 3 external to (shown above) the prisms 2, 2' and in front of the same to direct light to the area in front of the prisms 2, 2'. An inclined one-way mirror 4 is shown mounted in that area, forward of the prisms 2, 2' (or a mirror centrally apertured) to prevent obstructing the vision or fields of view established by the prisms 2, 2', while directing light, as at L, down the channel C parallel to and along and within the paths 20, 20'. The examiner thus looks either through the one-way mirror 4 (or the before-mentioned central aperture therein, not shown) and also through the center of the cone of light from the source 3 as reflected forward at L down the channel C, with light-focussing established in the usual well-known manner. By this construction, no parallax occurs between the light and the field of vision; and objects or parts in the narrow and/or deep tubular channel or cavity of the body C are examined stereoscopically as the light L is reflected therefrom back along the channel and paths 20, 20'. With the optical and illumination components mounted on and supported by a headgear 8, FIG. 3, with appropriate supporting struts 8' and elevated lamp and its power cord 3', a high degree of portability is achieved and with the examiner's hands totally free for surgery, manipulation, etc.

By inserting various magnifying loupes M between the eyes and the prisms 1, 1', FIG. 2, closer illuminated stereoscopic examination down the channel is readily available.

While the invention has been described particularly for use with body channels, the technique underlying the invention is also useful for providing three-dimensional viewing along other types of narrow and/or deep channels or tubes or similar structures. Other types of illuminating sources and refracting or reflecting components than illustratively shown may also be used; and further modifications will occur to those skilled in this art, such being considered to fall within the spirit and scope of the invention as defined in the appended claims.

I claim:

1. An instrument for illuminated stereoscopic examination of body cavities and the like, comprising a source of light, an optical system, and headgear means for supporting said source of light and said optical system on the head of an examiner, said optical system including means for directing a cone of light from said source away from the head of the examiner and toward a body cavity along a path substantially midway between the eyes of the examiner, means for splitting light reflected from said body cavity toward the head of the examiner along said path into two beams of light, means for directing said two beams of light toward the eyes of the examiner, respectively, said source of light being disposed relative to sad optical system so as to avoid obstruction of the examiner's view of said body cavity through said optical system, and means for positioning said cone of light directing means and said light splitting means so that the examiner's view of said body cavity is along the center of said one of light in both horizontal and vertical planes extending between the examiner and the body cavity.

2. An instrument in accordance with claim 1, wherein said means for splitting light reflected from said body cavity into two beams of light and said means for directing said two beams of light toward the eye of the examiner comprise prisms.

3. An instrument in accordance with claim 1, wherein said optical system includes loupe means for forming from said reflected light a magnified image of said body cavity.

4. An instrument in accordance with claim 1, wherein said source of light is supported offset from said path, and wherein said means for directing said cone of light from said source toward said body cavity comprises a mirror disposed on said path and constituting an optical component of said optical system that is closest to said body cavity.

5. An instrument for illuminated stereoscopic examination of body cavities and the like, comprising a source of light, an optical system, and headgear means for supporting said source of light and said optical system on the head of an examiner, said optical system including means for directing a cone of light from said source away from the head of the examiner and toward a body cavity along a path substantially midway between the eyes of the examiner, means for splitting light reflected from said body cavity toward the head of the examiner along said path into two beams of light, means for directing said two beams of light toward the eyes of the examiner, respectively, said source of light being disposed relative to said optical system so as to avoid obstruction of the examiner's view of said body cavity through said optical system, and means for positioning said cone of light directing means and said light splitting means so that the examiner's view of said body cavity is along the center of said cone of light, wherein said source of light is supported offset from said path, and wherein said means for directing said cone of light from said source toward said body cavity along said path comprises an optical component for redirecting light incident thereon from said source toward said body cavity along said path, said optical component being positioned farther from the head of the examiner, and closer to said body cavity, than said light splitting means and being constructed to pass light reflected from said body cavity to said splitting means.

* * * * *